US 6,716,238 B2

(12) United States Patent
Elliott

(10) Patent No.: US 6,716,238 B2
(45) Date of Patent: Apr. 6, 2004

(54) STENT WITH DETACHABLE TETHERS AND METHOD OF USING SAME

(75) Inventor: Christopher J. Elliott, Hopkinton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/852,524

(22) Filed: May 10, 2001

(65) Prior Publication Data

US 2002/0188341 A1 Dec. 12, 2002

(51) Int. Cl.$^7$ .................................................. A61F 2/06
(52) U.S. Cl. ...................................... 623/1.11; 623/1.12
(58) Field of Search ............................. 623/1.11, 1.12; 606/108

(56) References Cited

U.S. PATENT DOCUMENTS

| 5,019,085 | A | * | 5/1991 | Hillstead .................... 606/108 |
| 5,122,136 | A |   | 6/1992 | Guglielmi et al. |
| 5,354,295 | A |   | 10/1994 | Guglielmi et al. |
| 5,405,378 | A | * | 4/1995 | Strecker ........................ 623/1 |
| 5,423,829 | A |   | 6/1995 | Pham et al. |
| 5,749,921 | A |   | 5/1998 | Lenker et al. |
| 5,873,906 | A | * | 2/1999 | Lau et al. .................. 623/1.11 |
| 5,873,907 | A | * | 2/1999 | Frantzen .................... 623/1.11 |
| 5,882,335 | A |   | 3/1999 | Leone et al. |
| 5,891,128 | A |   | 4/1999 | Gia et al. |
| 5,941,888 | A | * | 8/1999 | Wallace et al. ............. 606/108 |
| 6,123,714 | A |   | 9/2000 | Gia et al. |
| 6,156,061 | A | * | 12/2000 | Wallace et al. ............ 623/1.11 |
| 6,168,616 | B1 | * | 1/2001 | Brown, III .................. 623/1.11 |
| 6,238,430 | B1 | * | 5/2001 | Klumb et al. ............... 623/1.11 |
| 6,254,612 | B1 | * | 7/2001 | Hieshima .................... 606/108 |
| 6,258,117 | B1 | * | 7/2001 | Camrud et al. ............. 623/1.16 |
| 6,261,305 | B1 | * | 7/2001 | Marotta et al. ............. 606/200 |
| 6,280,464 | B1 | * | 8/2001 | Hayashi ..................... 623/1.11 |
| 6,280,465 | B1 | * | 8/2001 | Cryer ......................... 623/1.11 |
| 6,350,277 | B1 | * | 2/2002 | Kocur ......................... 623/1.11 |
| 6,416,536 | B1 | * | 7/2002 | Yee ............................ 623/1.11 |
| 6,579,308 | B1 | * | 6/2003 | Jansen et al. ............... 623/1.15 |
| 2002/0038132 | A1 | * | 3/2002 | Abrams ...................... 606/200 |
| 2002/0151955 | A1 | * | 10/2002 | Tran et al. .................. 623/1.12 |

* cited by examiner

*Primary Examiner*—David H. Willse
*Assistant Examiner*—Javier G. Blanco
(74) *Attorney, Agent, or Firm*—RatnerPrestia

(57) ABSTRACT

A stent delivery system comprising a stent and at least one tether detachably connected to the stent by a connecting member. In one embodiment, the tether may comprise a conductive material and the connecting member may comprise a material subject to degradation upon application of an electrical current. In another embodiment, the connecting member, the stent, and the tether each may have a mechanical strength, where the strength of the connecting member is less than the strength of the stent and the tether. In yet another embodiment, application of electrical current may weaken the connecting member sufficient to enable detachment of the tether. A method of deploying a stent uses the stent delivery device comprising a tether attached to the stent by a connecting member. The tether may be used for accurate positioning of the stent.

28 Claims, 6 Drawing Sheets

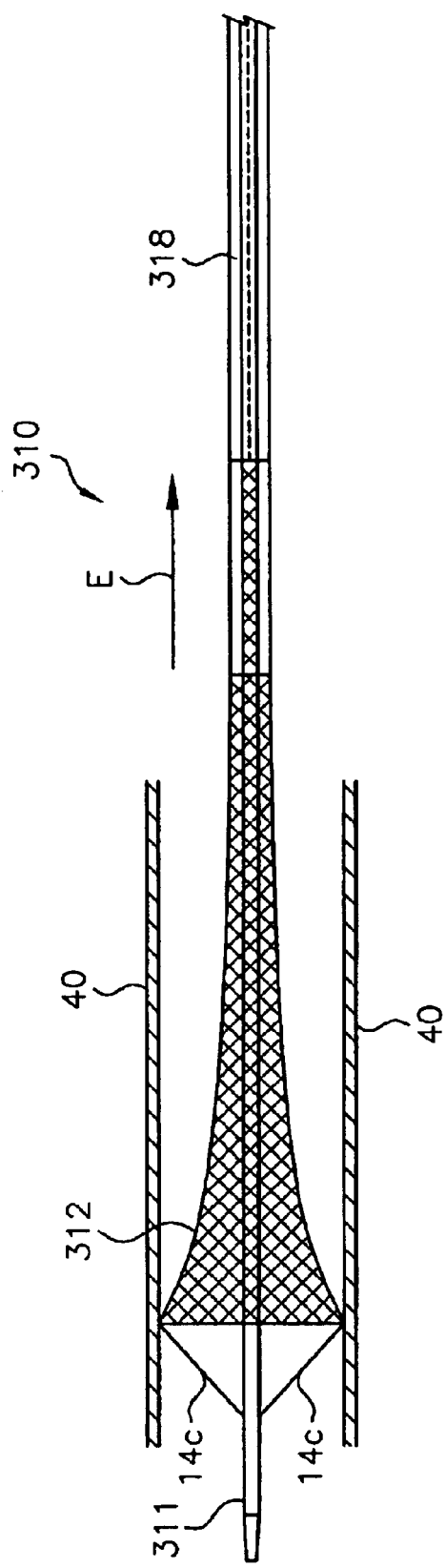
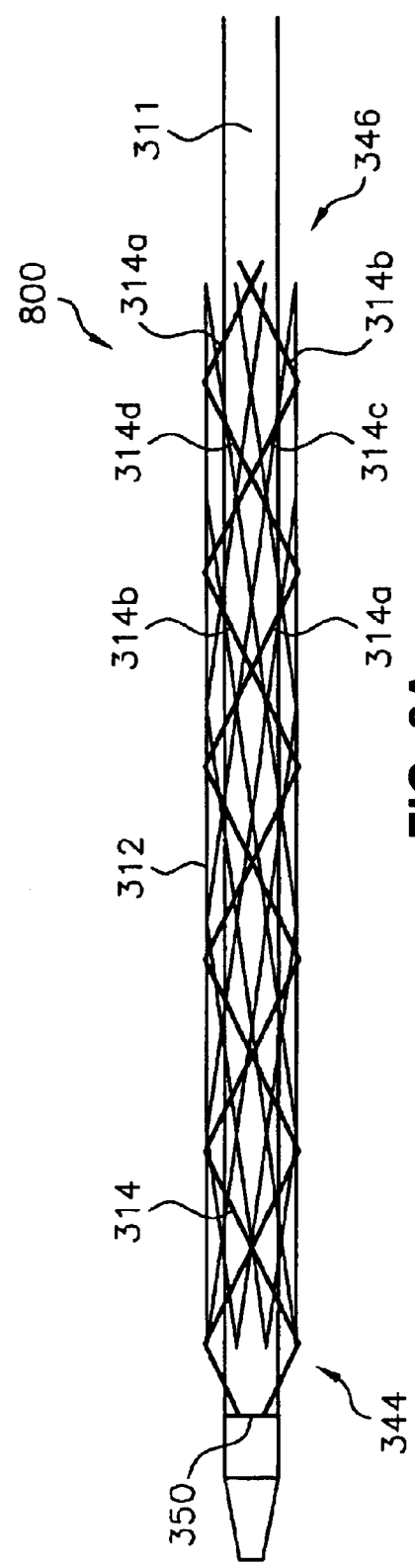
FIG. 7
FIG. 8A

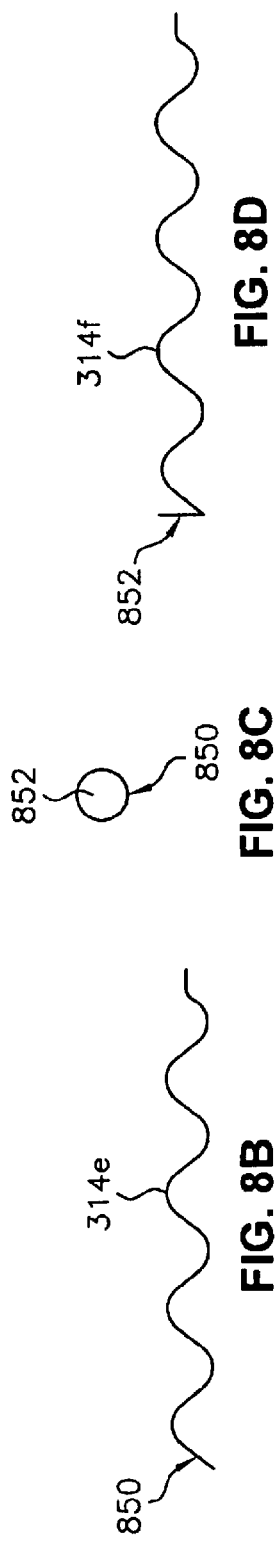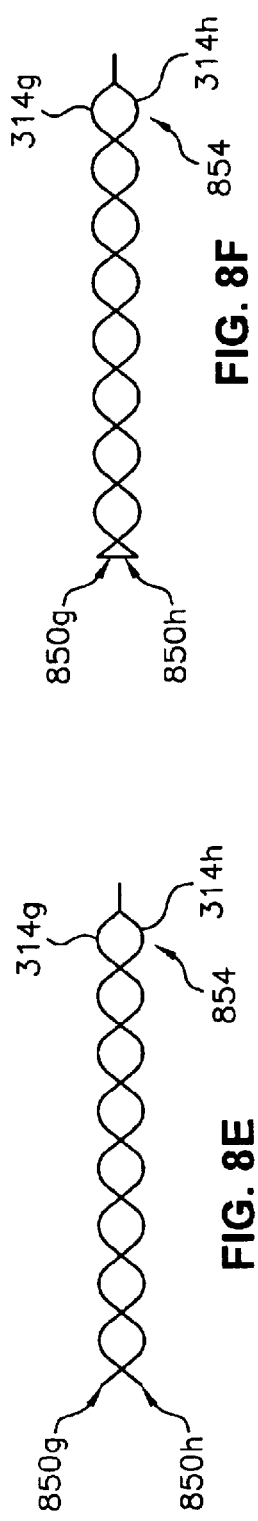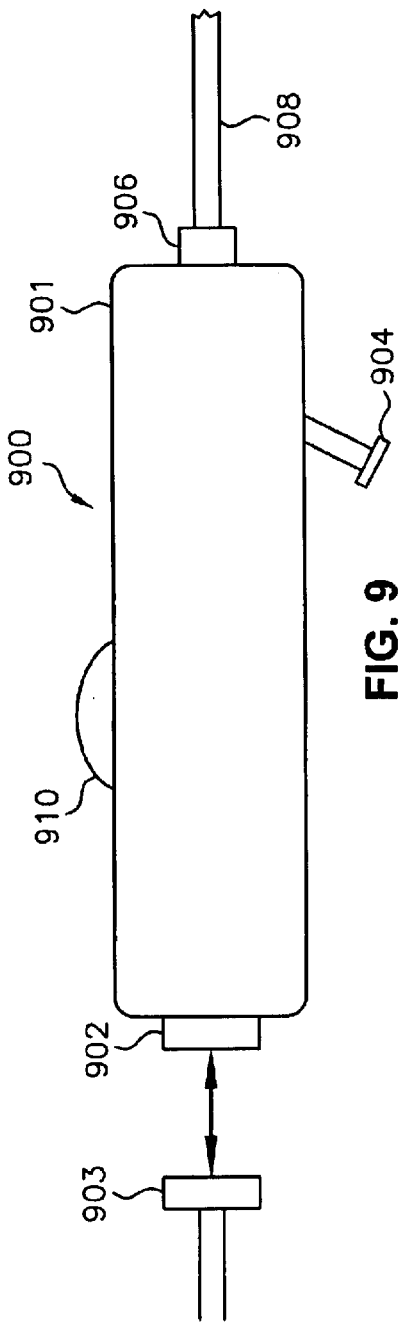

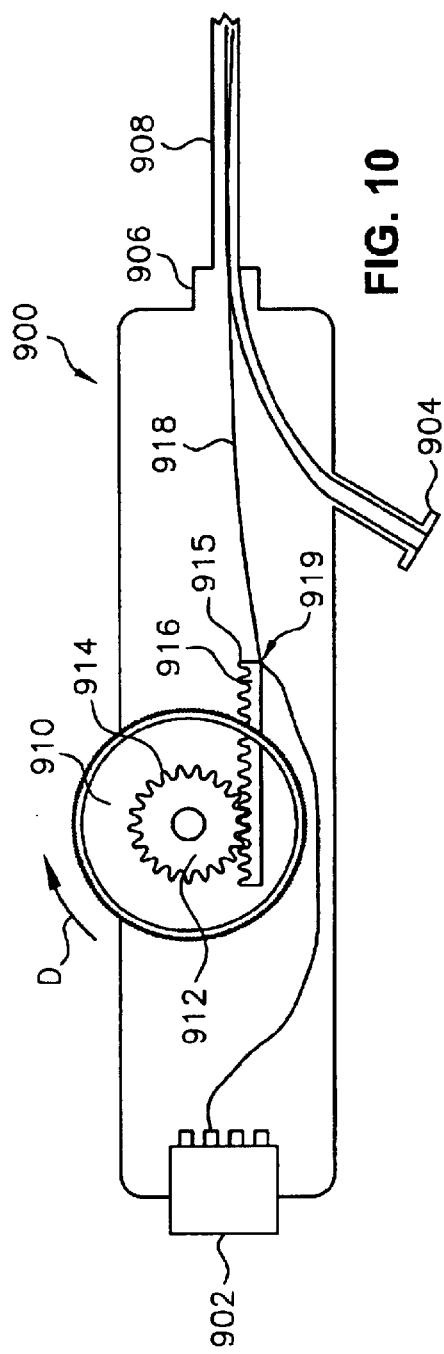
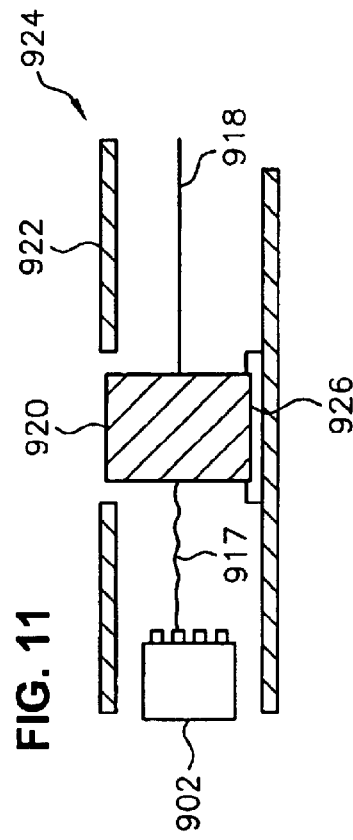
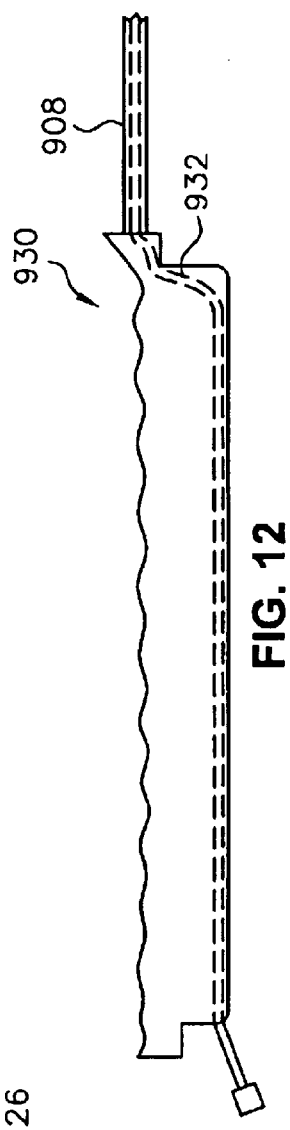

STENT WITH DETACHABLE TETHERS AND METHOD OF USING SAME

TECHNICAL FIELD

This invention relates generally to endoluminal grafts or "stents" and, more specifically, to stent delivery systems and methods.

BACKGROUND OF THE INVENTION

A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft. As used herein, however, the term "stent" is a shorthand reference referring to a covered or uncovered such device.

A covered stent may be used, for example, to treat a vascular aneurysm by removing the pressure on a weakened part of an artery so as to reduce the risk of rupture. Typically, a stent is implanted in a blood vessel at the site of a stenosis or aneurysm endoluminally, i.e. by so-called "minimally invasive techniques" in which the stent, restrained in a radially compressed configuration by a sheath or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means. The term "proximal" as used herein refers to portions of the stent or delivery system relatively closer to this access location, whereas the term "distal" is used to refer to portions farther from the access location.

When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

For a self-expanding stent, the delivery system typically comprises at least an outer sheath, the compressed stent within the outer sheath, and a stabilizer proximal of the compressed stent. The delivery system may further comprise an inner member that runs through the compressed stent and that attaches to a catheter tip distal of the stent. The term "stabilizer" is used in the art to describe a component of stent delivery systems used to stabilize or prevent retraction of the stent when the sheath is retracted. The stabilizer thus effects deployment of the stent into a desired location by forcing relative movement between the sheath and the stent. A stabilizer handle is typically located at the proximal end of stabilizer, outside the body lumen. To deploy the stent, the delivery system is threaded through the body lumen to a desired location for stent deployment. The outer sheath is then retracted, and the stabilizer prevents the stent from retracting proximally along with the sheath. As soon as the outer sheath constraining the stent is retracted, the stent typically expands into place.

For a balloon-expandable stent, the stent delivery system typically comprises the compressed stent preloaded around an inflatable balloon. The stent and underlying balloon are navigated to the desired deployment location and then the balloon is inflated to expand the stent into place.

In other embodiments, balloon-expandable or self-expanding stents may be used with a guide catheter which is first navigated through the lumen, such as over a guide wire, until its distal end is adjacent a deployment location. The guide catheter is then used as an outer sheath through which the stent is threaded. In such configurations, balloon-expandable stents have been known to come uncoupled from their underlying balloon inside the guide catheter, requiring that the entire catheter be removed and discarded.

With both self-expanding and balloon-expandable stents, the expansion process may cause unwanted movement of the stent. For example, with a balloon expandable stent, the proximal end of the balloon may inflate first. This may be due to, among other things, the location of the inflation lumen orifice (which may be at the proximal end of the balloon), variations in the stent geometry or in the crimping force used to compress the stent, variations in the folds of the balloon, and/or compressible air bubbles due to an incomplete balloon air purge prior to inflation with a non-compressible fluid. The result may be momentary instability in the stent position on the balloon, where axial force from the inflating balloon may overcome static friction between the balloon surface and the stent, resulting in axial migration of the stent. The axial migration may result in inaccurate deployment or outright embolization of the partially deployed stent.

Stents may also be shorter in their expanded configuration as compared to their compressed configuration. Thus, the expansion process may also cause the stent to shorten as its diameter expands. This shortening may also undesirably move the stent relative to its desired deployment position. The accurate placement of self-expanding stents may also be jeopardized during the deployment process.

Accurate placement of stents, especially short stents, such as used to repair ostial lesions, is important. For example, in ostial lesions of the renal arteries, stent misplacement can result in complications including a necessity for additional stent placement, stent migration and retrieval from the distal aorta, and renal failure. Given the importance of accurate stent placement in certain applications, an improvement to currently-available stents and stent delivery systems is desired.

SUMMARY OF THE INVENTION

In accordance with this invention, there is provided a stent delivery system comprising a stent and at least one tether detachably connected to the stent by a connecting member. The tether may connect to the stent in a proximal, distal, or medial location, and the stent may be balloon-expandable or self-expanding.

In one embodiment, the tether may comprise a conductive material and the connecting member may comprise a material subject to degradation upon application of an electrical current, such as a material that corrodes preferentially relative to the tether material. For example, the tether may comprise an insulated wire and the connecting member may comprise an uninsulated portion of the tether wire. In another embodiment, the connecting member may comprise a solder, a brazing paste, or an adhesive that has an impedance higher than the impedance of the tether.

In another embodiment, the connecting member, the stent, and the tether each have a mechanical strength, where the strength of the connecting member is less than the strength of the stent and the tether. The connecting member may have a first mechanical strength prior to application of electrical current and a second mechanical strength after application of an electrical current of sufficient magnitude and duration to degrade the first mechanical strength such that the second mechanical strength is less than both the mechanical strength of the tether and the mechanical strength of the stent. The connecting member may comprise a cross-sectional area that is smaller than the cross-sectional sectional areas of the tether and the stent.

The invention also comprises a method of deploying a stent using the stent delivery device comprising a tether attached to the stent by a connecting member. The method comprises the steps of inserting the stent delivery device into a lumen through an access location; navigating the stent delivery device to a deployment location; expanding the stent from a compressed configuration to an expanded configuration while using the tether to maintain the stent in the deployment location; and detaching the tether from the stent. The method may comprise repositioning or reconstraining the stent using the tether once the stent is in an expanded or partially-expanded configuration. Detaching the tether may comprise applying an electrical current to the tether that causes the connecting member to degrade, applying a tensional or torsional force to the tether that causes the connecting member to detach, or a combination thereof.

BRIEF DESCRIPTION OF THE DRAWINGS

FIG. 7 is a side view illustration of an exemplary stent delivery system of the present invention and a partial cross-section of a lumen showing a self-expanding stent in a partially deployed configuration.

FIG. 8A is a side view illustration of an exemplary low-profile stent delivery system using tethers rather than an outer sheath to constrain a self-expanding stent.

FIG. 8B is a side view illustration of another exemplary low-profile stent delivery system having a single tether attached to the stent.

FIG. 8C is an end view illustration of the distal end of the embodiment shown in FIG. 8D.

FIG. 8D is a side view illustration of yet another exemplary low-profile stent delivery system using a single tether that is attached to itself at its distal end.

FIG. 8E is a side view illustration of an exemplary low-profile stent delivery system using two tethers attached to the stent.

FIG. 8F is a side view illustration of another exemplary low-profile stent delivery system having two tethers attached to one another at their distal ends.

FIG. 9 is a side view illustration of an exemplary handle configuration.

FIG. 10 is a sectional view illustration of the handle of FIG. 9.

FIG. 11 is a sectional view illustration of another exemplary handle configuration.

FIG. 12 is a sectional view illustration of yet another exemplary handle configuration.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1:
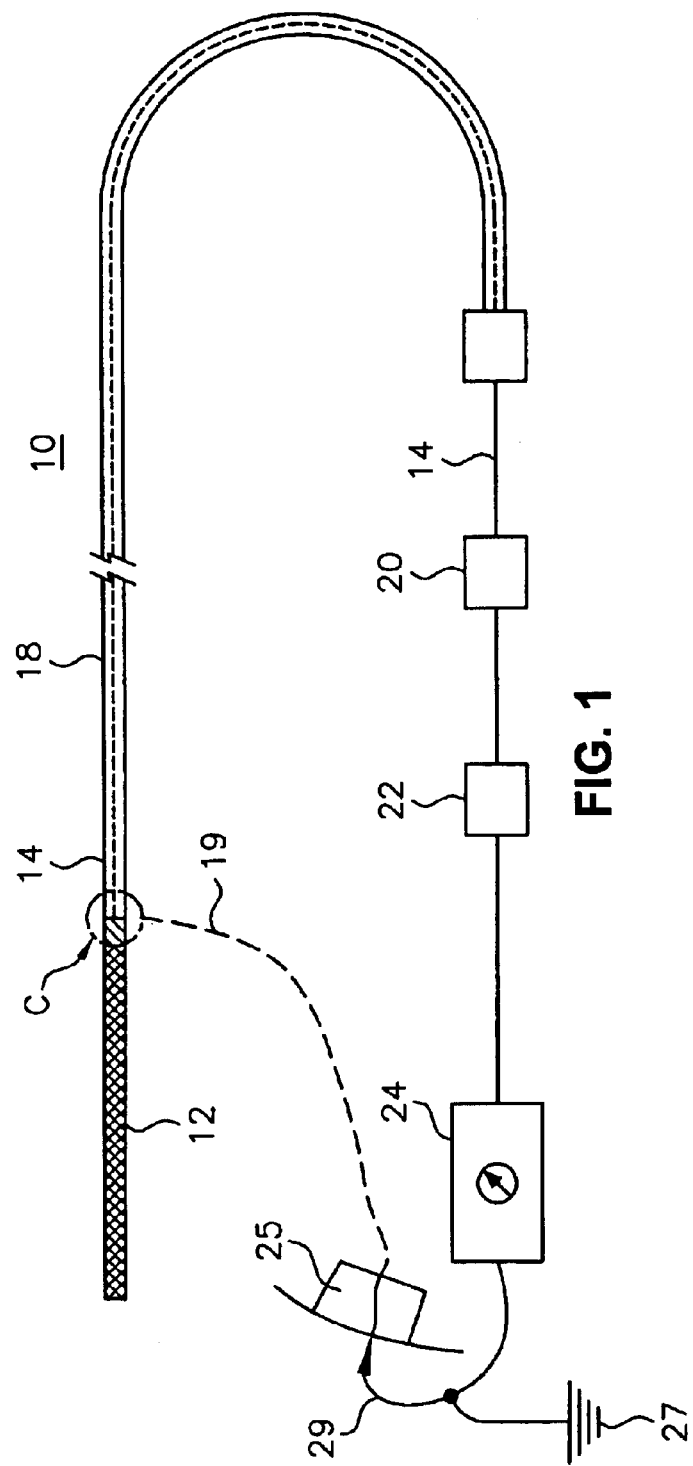
FIG. 1 is a side view illustration of an exemplary stent delivery system of the present invention.
Figure 2:
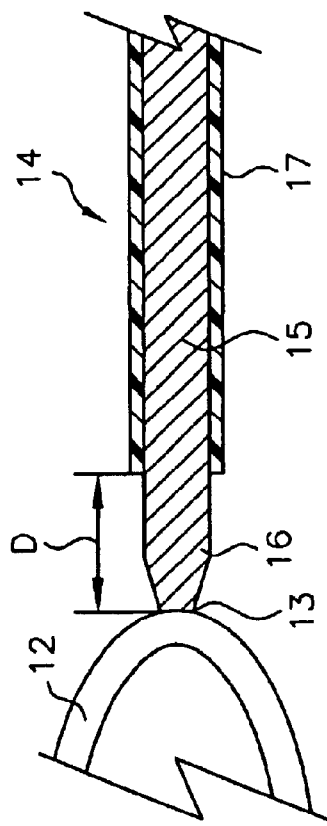
FIG. 2 is a cross-sectional illustration of an exemplary detailed portion of the encircled portion of the stent delivery system depicted in FIG. 1, showing a tether wire directly attached to the stent.
Figure 3:
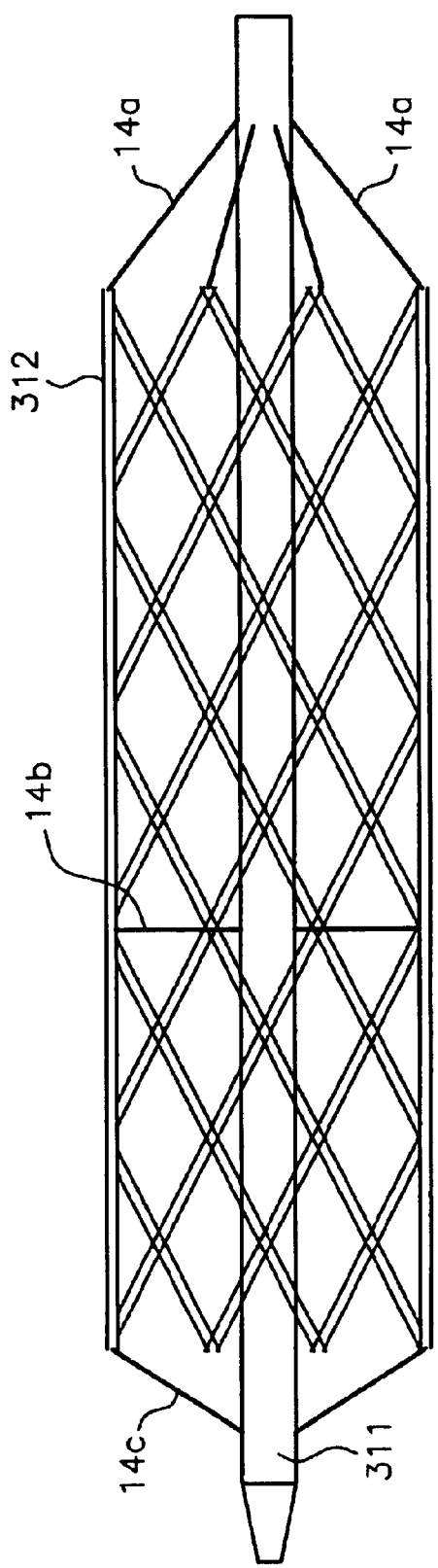
FIG. 3 is a side view illustration of an exemplary stent and stent delivery system depicting multiple tethers.

Referring now to FIGS. 1–3, one embodiment of the invention comprises a stent delivery system 10 comprising a stent 12 and at least one tether 14 detachably connected to the stent by a connecting member 16. Stent 12 may be balloon-expandable or self-expanding. The tether diameter (or thickness, for non-circular cross-sections) may for example be in a range of 0.003 to 0.010 inches, such as about 0.005 inches. Although shown in FIGS. 1 and 2 with a single tether 14 attached in a proximal location, FIG. 3 illustrates an embodiment comprising multiple tethers: a proximal tether 14a, a distal tether 14c, and a medial tether 14b. Embodiments comprising single or multiple tethers in any one of the proximal region 320, distal region 322, or medial region 324 of stent 312 shown in FIG. 3 as well as any combinations of single or multiple tethers in more than one of the regions may be provided.

As shown in FIG. 1, system 10 may comprise a withdrawal handle 20 connected to a proximal end of tether 14. Withdrawal handle 20 may be used to manipulate tether 14, for example to move the attached stent during deployment, to apply a force sufficient to break connecting member 16, or to retract the tether within delivery catheter 18 prior to removing the delivery catheter from the body. Handle 20 may comprise any sort of mechanical configuration known in the art for manipulating a cord or line to transmit tension and/or torque, and may range from an embodiment as simple as a loop in the wire through which a single finger may be placed, to more complex embodiments such as are described herein below.

System 10 may also comprise an electrical connector 22 that connects tether 14 to a power supply 24, such as a 9-volt battery. In one exemplary embodiment, tether 14 comprises a conductive material and connecting member 16 comprises a material subject to degradation upon application of an electrical current. The power supply provides an amount of voltage to supply enough current to cause connecting member 16 to degrade within a desired amount of time while not jeopardizing patient safety. For example, a range of about 2.5 to about 3.5 volts of direct current (DC) may be sufficient to maintain about 1 mA of current to achieve detachment of a tether of about 0.005 inch diameter within about 1 minute. The current then passes through the patient's body (dashed line 19) and exits the body through grounding patch 25, which is connected to ground 27 via electrode 29. The grounding patch may be any such patch known in the art, but depending on the amount of current, may desirably be of sufficient surface area to ensure physiologically insignificant current density at the current exit site. Instead of a grounding patch, a hypodermic needle (not shown) inserted under the patient's skin and connected to ground may also be sufficient, as is known in the art.

As shown in FIG. 2, which depicts one embodiment of the portion of FIG. 1 shown encircled by circle C, tether 14 may comprise a wire 15 having a coating of insulation 17, where connecting member 16 may comprise an uninsulated portion of wire 15. In this embodiment, tether 14 is electrically insulated to a point at a predetermined distance D from where it attaches to the stent. For example, in one embodiment, distance D may be on the order of about 0.005 inches. As shown in FIG. 1, tether 14 attaches to stent 12 by a solderless connection such as resistance welding or crimping. To detach the tether, current from the power supply passes through the connecting member 16 at a relatively high current density. To accentuate the current density, the distal end 13 of connecting member 16 may be tapered, as shown in FIG. 2, so that the cross-sectional area at the point of attachment to the stent is less than for the rest of tether 14.

Figure 4:
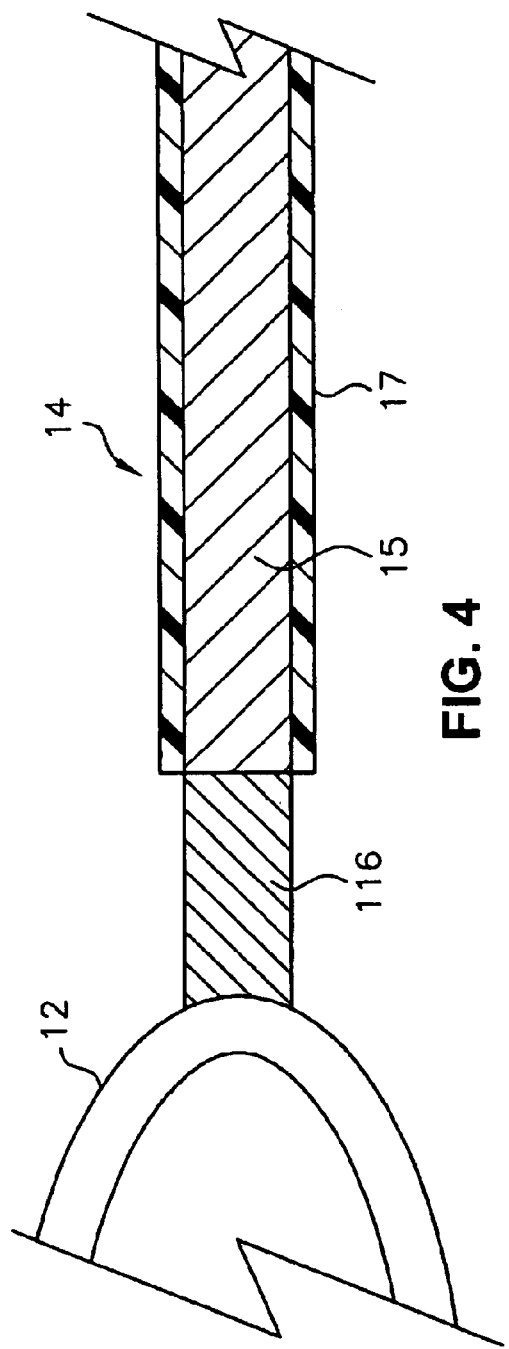
FIG. 4 is a cross-sectional illustration of an exemplary detailed portion of the encircled portion of the stent delivery system depicted in FIG. 1, showing a tether wire attached to the stent via an intermediate connection.

In one embodiment, the detachment process relies upon electrolytic corrosion. Thus, connecting member 16 may comprise any material that electrolytically corrodes preferentially relative to the stent material when energized with a current. For example, as shown in FIG. 4, connecting member 116 may comprise a different material from wire 15, such as but not limited to, solder, brazing paste, or an adhesive. By "electrolytically corrode preferentially" it is meant that the materials of the connecting member occupy a less noble (more anodic) position on the Galvanic scale relative to the portion of the stent to which the tether attaches. More anodic metals will corrode preferentially when placed adjacent more noble metals. For example, in the embodiment shown in FIG. 2, stent 12 may comprise platinum whereas wire 15 comprises passive or active stainless steel, or the stent may comprise a passive (more noble) stainless steel while the wire comprises active (more anodic) stainless steel.

Table 1 below lists a number of materials frequently used in medical applications in a generally accepted order from more noble at the top to more anodic at the bottom, as determined in flowing seawater. Items in parenthesis are based upon testing in a normal saline solution at 37 C, and placed in the series in accordance with expert opinion. Some resources may show a different order with respect to some of the materials, such as for example Ni—Cu alloys and 304 Stainless Steel. The specific order of materials provided here is merely exemplary and is not intended to be limiting in any way.

TABLE 1

MORE NOBLE
Graphite
Platinum
Ni—Cr—Mo Alloy C
Titanium
(Passivated nitinol)
(Elgiloy)
(316 Stainless Steel)
(Nitinol)
Nickel Copper Alloys
304 Stainless Steel
Silver TABLE 1-continued Nickel
Lead
Stainless 403
Nickel Silver
Brass
Copper
Low Carbon Steel
Zinc
MORE ANODIC Detachment may also rely upon high current density alone. For example, the stent may possess an electrically insulating coating or covering (not shown) but not at the metal-to-metal connection with connecting member 16. The coating or covering effectively prevents current flow from the stent into the body. In such case, current is forced to pass through connecting member 16 into the surrounding bloodstream before ultimately exiting the body. In such case, the high current density alone may be sufficient to degrade connecting member 16 or 116. The coating on the stent may comprise solely an electrical insulation, or may be a coating which serves multiple purposes, such as for providing drug delivery, for exclusion of restenosis, aneurysm exclusion, or any type of coating known in the art.

Where the connecting member is not a part of the wire, such as is shown in FIG. 4, the connecting member may have an impedance higher than the impedance of the wire. For example, the wire may comprise a copper-monel alloy and the connecting member may comprise solder or adhesive with a melt point below that of the surrounding metals.

Figure 5:
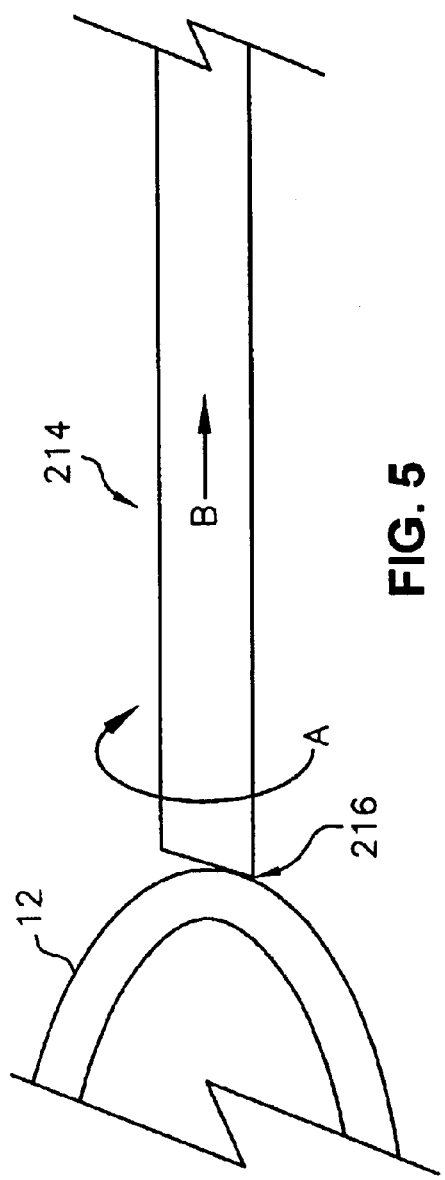
FIG. 5 is a cross-sectional illustration of an exemplary detailed portion of the encircled portion of the stent delivery system depicted in FIG. 1, showing a tether wire attached to the stent by a connection designed to be mechanically broken.

Referring now to FIG. 5, there is shown another embodiment in which effecting some mechanical failure is used to achieve the purpose of the invention. This may be done in a number of ways. For example, connecting member 216 between tether 214 and stent 12 may have a cross sectional area that is less than the cross-sectional area of the tether or the stent. Connecting member 216 therefore has a mechanical strength that is less than the strength of tether 214 and stent 12. Tether 214 may have high torque transmission capability, such that if the tether is twisted at its proximal end, its distal end also twists along arc A (or in the opposite direction), and the lesser torsional strength of connecting member 216 causes it to break before the tether or stent 12. The connecting member may also be sufficiently weak to enable detachment by applying sufficient tension along arrow B. Because it may sometimes be desirable to apply tensional forces on tether 214 to manipulate stent 12, however, the tensile strength of connecting member 216 may be sufficiently strong to allow reasonable manipulation without breaking, but sufficiently weak to promote breaking when desired. For this reason, a connecting member 216 that has relatively strong tensile strength and relatively weaker torsional strength may be used and the application of torsional forces avoided until it is desired for the connecting member to detach. In yet another embodiment, the mechanical failure may be brought on by compressive or flexural forces, such as by pushing on tether 214 in the direction opposite arrow B to cause the tether to flex at connecting member 216 and break.

One exemplary embodiment may comprise the principles illustrated in both FIGS. 2 (or 4) and 5. In such an embodiment, the connecting member has a first mechanical strength prior to application of any electrical current and a second, lesser mechanical strength after application of an electrical current of sufficient magnitude and duration to degrade the first mechanical strength. Thus, although the connecting member may be equally strong as or stronger than the stent and/or tether prior to application of any current, after application of the electrical current, the connecting member is weaker than both the tether and the stent. The connecting member may be weaker tensionally, torsionally, or a combination thereof.

To facilitate detachment of the connecting member, any number of handle embodiments may be used. Exemplary handle configurations are shown in FIGS. 9–12 for illustration without limitation. FIG. 9 illustrates a handle 900, which comprises a body 901, an electrical connection 902 to a power supply cable 903, and an adapter 904, such as a Luer Adapter for connection to balloon inflation means. Handle 900 is connected to catheter 908 via strain relief connection 906 as is known in the art. Handle 900 further comprises a tether retraction wheel 910, which may be knurled or in the shape of a gear to provide traction for the user's finger. As shown in FIG. 10, wheel 910 may be stationary and coaxial with a pinion 912. Pinion 912 has teeth 914 that mesh with corresponding teeth 915 of axially movable rack 916. Rack 916 is attached to tether wire 918 with a connection 919 that can withstand the tensile forces encountered during subsequent retraction of the tether. Connection 919 serves to take the strain of such tensile forces rather than such forces being transmitted to the connection with the power source. In use, electricity is sent down tether wire 918 to weaken the connection (not shown) between the tether and the stent, and then wheel 910 is turned in the direction of arrow D to retract rack 916 which in turn retracts tether wire 918 with sufficient force to break the connection.

In another embodiment, shown in FIG. 11, the mechanism for separation of the tether may impart a torsional force. Wheel 920 comprises a spiral gear adapted to rotate coaxial with or parallel to the axis of handle 924. Spirally geared wheel 920 protrudes from body 922 of handle 924, meshes with a fixed rack 926, and is connected to tether wire 918. Thus, after the electrical current is transmitted through tether wire 918, the user may rotate spiral gear 920 so that the gear moves proximally (toward electrical connector 902), imparting both a torsional and tensional force on the connecting member (not shown). Proximal portion 917 of tether wire 918 proximal of spiral gear 920 may have sufficient slack to provide strain relief such that the torsional forces imparted on portion 917 as a result of the rotation of wheel 920 are insufficient to break that portion. Rather than comprising a spiral gear that imparts both tensional and torsional force, wheel 920 may instead freely rotate to impart a torsional force alone without a rack. In both the embodiments shown in FIGS. 9–11, racks 916 and 926, respectively, may be long enough not only to transmit tensile forces to detach the connecting member, but also long enough to retract the tether into a desired position for retraction of the delivery system from the body lumen without risk of the loose tether causing damage.

In yet another embodiment, shown in FIG. 12, handle 930 may simply comprise a manipulation rod 932, which may be the proximal end of a pusher or stabilizer rod and/or the proximal end of inner member 311 shown in FIG. 3. Thus, for example, manipulation rod 932 may be first used as a stabilizer during deployment of a self-expanding stent when an outer sheath is retracted, then used for recapture of a partially deployed stent or repositioning of a partially or fully deployed stent, if desired, and then used for detaching one or more connecting members (not shown) and/or retracting one or more tethers attached at or near the distal end of the rod (not shown). Manipulation rod 932 may be rotated and/or pulled axially to detach the connecting member, for example after application of electrical current has at least weakened the connecting member. When the electrical force is sufficient to sever the connecting member without additional mechanical force, rod 932 is used for proximally retracting the tether within the sheath for removing the sheath from the body.

Although handle 930 is shown in FIG. 12 without a connection to an inflation means and without an accompanying electrical connection for simplicity of illustration, the manipulation rod embodiment may be combined with elements of any of the other embodiments shown and described herein. In fact, any of the elements of any of the handle embodiments shown herein may be combined with one another or with other elements known in the art, as desired. The handle embodiments shown herein are some of the numerous possibilities available to exert the desired forces on the tethers, and any handle embodiment may be used. The handles may be used to sever connections and/or to retract tethers connected to the stent itself, to each other, or to another element in a tether system.

Although described herein with respect to one embodiment for detachably connecting the tethers to the stent, the attachment mechanism for attaching the tethers may be any mechanism known in the art. Other suitable mechanisms for detachably connecting a wire to an implantable device are described in U.S. Pat. Nos. 5,354,295 and 5,122,136 to Guglielmi et al., both of which are incorporated herein by reference.

Figure 6:
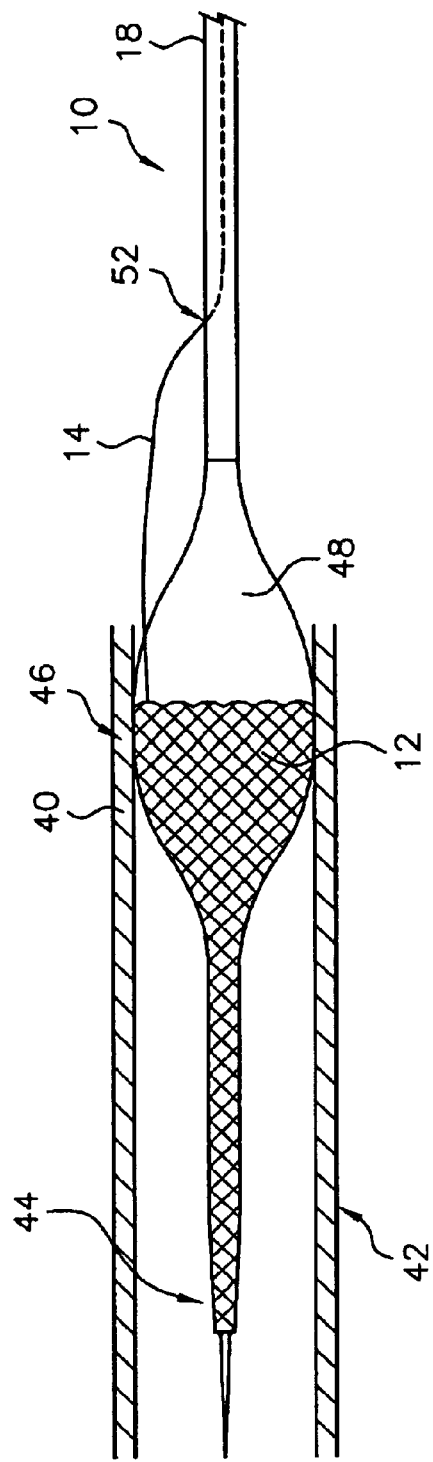
FIG. 6 is a side view illustration of an exemplary stent delivery system of the present invention and a partial cross-section of a lumen showing a balloon-expandable stent in a partially deployed configuration.

The stent delivery systems described herein may be used in a method for deploying a stent having attached tethers. As illustrated in FIG. 6, the method comprises the steps of inserting the stent delivery device 10 into a lumen 40 through an access location (not shown) and navigating the stent delivery device to a deployment location 42. Stent 12 is then expanded from a compressed configuration (shown at distal end 44) to an expanded configuration (shown at proximal end 46) while using tether 14 to maintain the stent in the deployment location. Although shown in FIG. 6 being expanded using a balloon 48 connected through catheter 18 to inflation means, stent 12 may also be a self-expanding stent. Tether 14 is then detached from the stent by exerting a torsional or tensional force, by applying an electric current, or some combination thereof, as described above. After detachment of the tether from the stent, the detached tether may be retracted into the delivery device, and the delivery device removed from the lumen.

As shown in FIG. 6, tether 14 runs inside catheter 18 until an exit point 52 proximal of balloon 48. Locating the exit point proximal to balloon 48 in a balloon-expandable system is desirably because the relatively high balloon deployment pressures benefit from an intact balloon surface having no perforations.

Referring now to FIG. 7, for a self-expanding stent 312, stent delivery device 310 typically comprises an outer sheath 318 and an inner member 311. One or more distal tethers 14c may be used to prevent proximal movement during retraction of outer sheath 318 in the direction of arrow E. Tethers may thus facilitate low-profile delivery systems that eliminate standard stabilizers (not shown) commonly used to prevent proximal retraction of the stent during retraction of outer sheath 318. As shown in FIG. 3, the stent may also have proximal tethers 14a to prevent the stent from jumping distally or embolizing during deployment. Proximal tethers 14a may also be used for repositioning or reconstraining the stent once the stent is in an expanded or partially-expanded configuration. For example, after stent 312 has been partially deployed, even more than 90% deployed from outer sheath 318 (shown in FIG. 7), tethers 14a may be used for pulling the stent back into the sheath. For such applications, however, the tethers may be detachable by some means other than tensile forces alone, as application of substantial tensile force may be transmitted to reconstrain the stent. Self-expanding stent systems may comprise proximal tethers only, distal tethers only, or a combination thereof.

Referring now to FIG. 8A, instead of having an outer sheath 318 as shown in FIG. 7, a low-profile stent delivery system 800 for a self-expanding stent 312 may comprise the stent being held in place on inner member 311 by one or more tethers 314 wrapped around the stent to keep it from expanding. For example, four tethers 314a–d may each be wrapped helically around stent 312. The helically wrapped tethers 314a–d may comprise two wrapped in one helical orientation (clockwise) and the other two wrapped in the opposite helical orientation (counter-clockwise), as shown in FIG. 8A, or the tethers may be wrapped all in the same helical orientation. The tethers may exit the inner member 311 through a single hole or through multiple, equally spaced holes (90 degrees apart, as shown in FIG. 8A) at proximal end 346. At distal end 344 of stent 312, tethers 314a–d may connect to one another, to the distal end of the stent, or to a tether harness 350, such as a ring mounted to inner member 311, with a connecting member between at the end of each tether that allows detachment of the tether by any of the mechanisms discussed herein. When the stent has been delivered to the desired deployment location, the tethers are detached at the distal end by any of the mechanisms discussed herein, and the stent self-expands while unraveling the tethers. The unraveled tethers may then be fully retracted within inner member 311 or the inner member retracted within the outer sheath (not shown) so that the tethers do not come in contact with or snag the body lumen when the inner member is pulled back through the lumen. For the embodiments shown in both FIGS. 7 and 8A, the proximal end of inner member 311 may comprise any of the handle embodiments described herein.

Alternate arrangement of wrapped tethers are shown in FIGS. 8B–8F, which show the tethers without the underlying implants for simplicity of illustration. FIG. 8B shows a single tether 314e wrapped helically and adapted to be attached to the underlying stent at the distal end 850 of the tether. Instead of attaching to the underlying stent, tether 314f may instead make at least one circular revolution 852 and attach to itself at the distal end, as shown in FIGS. 8C and 8D. Circular revolutions of the tether with or without corresponding attachments to itself may also be provided at additional locations along the length of the stent as desired. Multiple tethers 314g and 314h may wind helically around the implant and attach to the implant at their respective distal ends 850g and 850h, such as shown in FIG. 8E, or may attach to each other, as shown in FIG. 8F. Any number of tethers may be used and any helical pitch (the number of revolutions per unit length) may be used. The tethers may attach to the implant or to each other at one or more points. Any of the connection points between one tether to itself or another, or between the tether and the stent shown in FIGS. 8A–8F may comprise any of the detachable connection types described herein for releasing the tethers when desired. Any of the tether systems shown in FIGS. 8A–8F may further be used in conjunction with any of the handles shown and/or described herein for breaking the connection point and retracting the tethers.

Although described above with respect to self-expanding stents, tethers wrapped externally around the stent may also be used with balloon-expandable stents. For example, use of externally-wrapped tethers around a balloon-expandable stent may allow delivery to an area such as the renal artery ostia without a guide catheter, reducing the overall system profile and enhancing stent security during delivery and deployment. The externally-wrapped tethers provide additional tip stiffness as compared to systems without such tethers. Thus, the arrangement may also allow a reduction in the profile of the catheter tube under the balloon. The externally-wrapped tethers essentially act as a temporary external scaffold to enhance mechanical properties of the stent with a reduction, or at least without any increase, in system profile and provide additional stent security. With such additional security, for example, a clinician may comfortably temporarily withdraw the guidewire to perform a radiopaque contrast injection to verify position prior to deployment, without concern that the system will move out of position or kink during guidewire removal.

In another embodiment, one or more additional tethers, such as one or more distal tethers 14a, medial tethers 14b, and/or proximal tethers 14c as shown in FIG. 3 and described infra may be attached to stent 312 and configured to detach subsequent to detachment of the tethers used to radially constrain stent 312. This may be accomplished by material selection or specific application of current. Wrapping tethers 314 attached to the stent may serve multiple purposes. For example, in the embodiments shown in FIG. 8E or 8F, the tethers may wrap around the stent and be attached to one another or to the stent at distal ends 850g and 850h and at least one of the tethers may also be connected to the stent at proximal end 854. Provision of a first amount of electrical current may be sufficient to detach the connection or connections at distal ends 850g and 850h, but not at proximal end 854. Thus, after providing a first amount of electrical current, the stent self-expands, but at least one of tethers 314g and 314h is still attached to the stent. The provision of a second amount of electrical current and/or the provision of a tensile or torsional force on the connected tether may then be required to detach the connection at proximal end 854. Multi-purpose tethers may be used with respect to any of the embodiments shown in FIGS. 8A–8F.

As shown in FIG. 3, a plurality of proximal tethers 14a may be desired, because of the forces transmitted during reconstrainment of stent 312. A plurality of tethers 14a provides not only a spreading of forces among a number of members, but also provides redundancy in case one or more tethers break unexpectedly. The advantages of spreading forces and providing redundancy are applicable to balloon-expandable stents also. For self-expanding stents, distal tethers 14a or medial tethers 14b may be contained within inner member 311 (shown in FIG. 7), exiting via an exit points 313 that enable application of the directional forces desired. Proximal tethers may be contained within outer sheath 318 outside of inner member 311, or may be contained within inner member 311 and exit at some point proximal to the stent.

The tethers may be used to hold the stent in place either absolutely (with no slack) or relatively (with some slack). Providing some slack may be desired, for example, to account for shortening of the stent upon deployment or to take into account heat-induced lengthening of the tethers during a sterilization step. As is well-known in the art, many stent architectures are prone to having a greater length in their compressed configuration than in their expanded configuration. Accordingly, positioning a stent with a high shortening ratio (the ratio of compressed length over expanded length) using tethers with no slack potentially may pull the stent toward the tethers as it expands. If it is desired to align a high-shortening-ratio stent while in its compressed configuration and use the tether to prevent the stent from moving its end point beyond some boundary, relatively more slack in the tether may be provided. If, on the other hand, it is desired to align the connecting member between the stent and the tether in the desired location taking into account the stent shortening, then less slack may be provided.

The stent delivery system and method of this invention are particularly useful for use in repairing ostial lesions of the renal arteries because of the acute desire for accurate stent placement in that application. The system and method are equally applicable, however, to any application where accurate deployment of a stent may be desired for any reason.

Although described herein with respect to use with stents, the tethers described herein may be used in conjunction with any implantable endoluminal devices, including but not limited to vena cava filters. Also, although use with balloon-expandable and self-expanding stents has been described herein, the tethers of this invention may also be used with hybrid balloon-expandable/self-expanding stents, such as for example the hybrid stents described in U.S. patent application Ser. No. 09/702,226 to Walak and assigned to the common assignee of this invention. Furthermore, although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A stent delivery system comprising a stent and at least one tether detachably connected to the stent by a connecting member, the tether comprising a conductive material and the connecting member comprises a material selected from a group consisting of: a solder, a brazing paste, or an adhesive, the material subject to degradation upon application of an electrical current, the conductive material of the tether comprising a wire having a first impedance, and the connecting member having a second impedance higher than the first impedance.

2. The system of claim 1 wherein the stent has a compressed configuration and an expanded configuration, the system further comprising a tubular delivery catheter having a distal portion on which the stent is axially mounted, and an outer sheath over the compressed stent and the delivery catheter, the connecting member comprising a portion of the tether wherein the tether is helically wrapped about the stent to hold the stent in the compressed configuration.

3. The system of claim 2 wherein an intermediate portion of the tether is contained within a proximal portion of the delivery catheter and exits the delivery catheter through an exit hole in the catheter proximal of the distal portion on which the stent is mounted, and a proximal end of the tether is connected to a tether handle located outside of the delivery catheter.

4. The system of claim 1 wherein the tether connects to the stent in a proximal location.

5. The system of claim 1 wherein the tether connects to the stent in a distal location.

6. The system of claim 1 wherein the tether connects to the stent in a medial location.

7. The system of claim 1 wherein said at least one tether comprises a plurality of tethers.

8. The system of claim 1 further comprising a handle attached to the tether for at least one of: assisting in detachment of the detachable connecting member and retracting the tether after detachment.

9. The system of claim 8 wherein the handle further comprises a stationary pinion and a movable rack attached to the tether, a fixed rack and a spiral gear attached to the tether, or a manipulation rod attached to the tether.

10. The system of claim 1 wherein the stent is a self-expanding stent or a hybrid self-expanding/balloon-expandable stent.

11. The system of claim 1 wherein the conductive material of the tether comprises a copper-monel wire and the material of the connecting member comprises a solder or an adhesive.

12. A method of deploying a stent using a stent delivery device comprising a tether attached to the stent by a connecting member, a tubular delivery catheter having a distal portion on which the stent is axially mounted, and an outer sheath over the compressed stent and the delivery catheter, the connecting member comprising (i) a portion of the tether wherein the tether is helically wrapped about the stent to hold the stent in the compressed configuration, (ii) a solder, a brazing paste, or an adhesive, wherein the tether comprises a conductive wire having a first impedance and the connecting member has a second impedance higher than the first impedance such that the connecting member is subject to degradation upon application of an electrical current, or (iii) a combination of (i) and (ii), the method comprising the steps of:

(a) inserting the stent delivery device into a lumen through an access location;

(b) navigating the stent delivery device to a deployment location;

(c) retracting the outer sheath and expanding the stent from a compressed configuration to an expanded configuration while using the tether to maintain the stent in the deployment location; and (d) detaching the tether from the stent.

13. The method of claim 12 wherein step (c) further comprises repositioning or reconstraining the stent using the tether once the stent is in an expanded or partially-expanded configuration.

14. The method of claim 12 wherein step (d) comprises applying an electrical current to the tether which causes the connecting member to degrade.

15. The method of claim 12 wherein step (d) further comprises applying an electrical current to the tether which causes the connecting member to degrade prior to applying a tensional or torsional force for causing the connecting member to detach.

16. The method of claim 12 further comprising the steps of:

(e) retracting the detached tether into the delivery device, and (f) removing the delivery device from the lumen.

17. The method of claim 12 wherein step (c) comprises self-expansion of the stent.

18. The method of claim 12 comprising deploying a stent to repair an ostial lesion.

19. A stent delivery system comprising a stent having a compressed configuration and an expanded configuration, at least one tether detachably connected to the stent by a connecting member, a tubular delivery catheter having a distal portion on which the stent is axially mounted, and an outer sheath over the compressed stent and the delivery catheter, the tether comprising a conductive material and the connecting member comprising a material subject to degradation upon application of an electrical current, the connecting member material comprising a solder, a brazing paste, or an adhesive, the conductive material of the tether comprising a wire having a first impedance, and the connecting member material having a second impedance higher than the first impedance.

20. The system of claim 19 wherein the tether connects to the stent in a proximal location.

21. The system of claim 19 wherein the tether connects to the stent in a distal location.

22. The system of claim 19 wherein the tether connects to the stent in a medial location.

23. The system of claim 19 wherein said at least one tether comprises a plurality of tethers.

24. The system of claim 19 further comprising a handle attached to the tether for at least one of: assisting in detachment of the detachable connecting member and retracting the tether after detachment.

25. The system of claim 19 wherein the stent is a self-expanding stent or a hybrid self-expanding/balloon-expandable stent.

26. The system of claim 19 further comprising a power supply connected to a tether.

27. The system of claim 26 wherein the power supply comprises a 9 V battery.

28. The system of claim 19 wherein an intermediate portion of the tether is contained within a proximal portion of the delivery catheter and exits the delivery catheter through an exit hole in the catheter proximal of the distal portion on which the stent is mounted, and a proximal end of the tether is connected to a tether handle located outside of the delivery catheter.

* * * * *